United States Patent [19]

Dick, Jr. et al.

[11] 4,146,650
[45] Mar. 27, 1979

[54] SUBSTITUTED BENZODIOXAN SWEETENING COMPOUND

[75] Inventors: William E. Dick, Jr., Washington; John E. Hodge, Peoria, both of Ill.

[73] Assignee: The United States of America as represented by the Secretary of Agriculture, Washington, D.C.

[21] Appl. No.: 900,373

[22] Filed: Apr. 26, 1978

[51] Int. Cl.² ............... A23G 3/30; C07D 319/08
[52] U.S. Cl. .................................. 426/3; 260/340.3; 426/548; 426/590
[58] Field of Search ............... 260/340.3; 426/548, 426/3, 590

[56] References Cited
U.S. PATENT DOCUMENTS 3,484,448  12/1969  Krämer .................. 260/340.3

Primary Examiner—Ethel G. Love
Attorney, Agent, or Firm—M. Howard Silverstein; David G. McConnell; Curtis P. Ribando

[57] ABSTRACT

A sweet compound, 2-(3-hydroxy-4-methoxyphenyl)-1,3-benzodioxan, and its salts have been prepared and are characterized by the following structural formula:

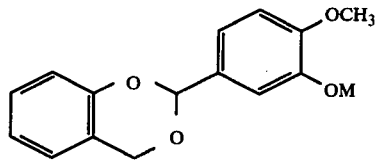

wherein M is hydrogen or a physiologically acceptable metal cation. This compound is intensely sweet, and is useful for sweetening foods and other ingestible substances.

9 Claims, No Drawings

SUBSTITUTED BENZODIOXAN SWEETENING COMPOUND

BACKGROUND OF THE INVENTION

1. Field of the Invention

This invention relates to a synthetic sweetening compound which resembles in both structure and flavor the naturally occurring phyllodulcin, a rare, intensely sweet isocoumarin derivative.

2. Description of the Prior Art

The present controversy over the healthfulness of dietary sweeteners underscores the need for a harmless, noncariogenic, intensely sweet, additive for dietary foods and pharmaceuticals. Some naturally sweet products of botanical origin, or derivatives prepared from such extracted products are known to have saccharin-like sweetness (J. E. Hodge et al., in "Symposium: Sweeteners," Inglett, G. E., ed., Avi Publishing Co., Westport, Conn., 1974, Chapter 20), but candidate compounds often have structures too complex for facile synthesis and are not isolated economically from agricultural sources. These limitations make it unlikely that a sweetener such as phyllodulcin [H. Arakawa et al., Chem. Ind. (London) 671 (1959) and Asahina et al., Ber. Dtsch. Chem. Ges. 64: 1252-1256 (1931)], an isocoumarin derivative isolated from *Hydrangea thunbergii Sieb.* and consumed as a tea-like decoction in Japan will be of commercial value, even though it is reported to be either 400 [M. Yamato et al., Chem. Pharm. Bull. 25: 695-699 (1977)] or 600-800 times sweeter than sucrose [Suzuki et al., Agric. Biol. Chem. 41(4): 719-720 (1977)]. A more likely source of suitable sweeteners will be synthetic compounds which are easily prepared and which contain the specific structural features of the natural model required for expression of sweetness.

SUMMARY OF THE INVENTION

We have now surprisingly found an intensely sweet synthetic compound which has certain structural similarities to phyllodulcin and mimics its sweet taste. This compound, 2-(3-hydroxy-4-methoxyphenyl)-1,3-benzodioxan, and its sweet salts are characterized by the following structural formula:

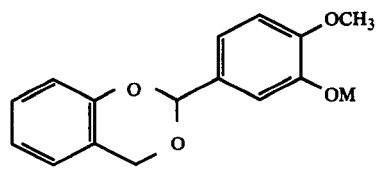

where M is hydrogen or a physiologically acceptable cation.

In accordance with this discovery, it is an object of the invention to prepare a sweetening compound which is easily synthesized and commercially promising.

It is also an object of the invention to prepare a dietary sweetener which is noncariogenic and generally harmless.

Another object of this invention is to provide a sweet additive for ingestible compositions including foods, beverages, chewing gums, and medicinal preparations.

Other objects and advantages of this invention will become readily apparent from the ensuing description.

DETAILED DESCRIPTION OF THE INVENTION

The sweetening compound of this invention is prepared from two well-known and naturally occurring compounds, 3-hydroxy-4-methoxybenzaldehyde (isovanillin) and o-hydroxybenzyl alcohol (salicyl alcohol). These compounds are reacted to form the isovanillin acetal, a 1,3-benzodioxan. Described below is an effective indirect route of synthesis employing an intermediate acetal.

Prior to the acetalization, the phenolic hydroxyl of the isovanillin is preferably blocked with either an alkyl or aromatic ester or else a benzyl ether. For example, the chloroacetoxy ester of isovanillin is easily prepared by reaction with chloroacetyl chloride. Of course, it is understood that any blocking agent of the above-mentioned etherifying or esterifying groups, which would protect the hydroxyl from entering into the subsequent acetalization reaction, could be substituted for chloroacetyl chloride.

Conversion of the isovanillin to an intermediate dialkyl acetal is then effected by any procedure as known in the art, such as by reacting the aldehyde with a trialkylorthoformate. Trimethylorthoformate and other lower alkyl reagents are preferred for the reason that the intermediate acetal substituents can be later recovered as distillable alcohols.

An acetal exchange reaction of the intermediate acetal with the salicyl alcohol yields the 1,3-benzodioxan derivative. If the phenyl hydroxyl was originally blocked with an ester, the blocking group is removed by saponification with alkali. The ethers can be catalytically hydrogenated to remove the blocking group.

It is anticipated that the isovanillin and salicyl alcohol will react directly, without going through the intermediate acetal. However, increased side reactions, decomposition, and reduced yields diminish the advantages of such a route.

The basic reaction sequence for the preparation of 2-(3-hydroxy-4-methoxyphenyl)-1,3-benzodioxan is illustrated as follows:

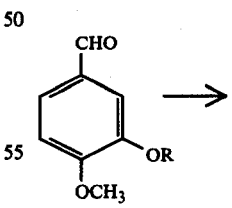

isovanillin (R = H)

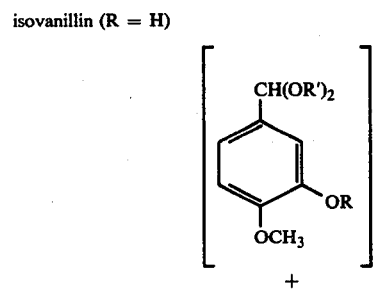

+

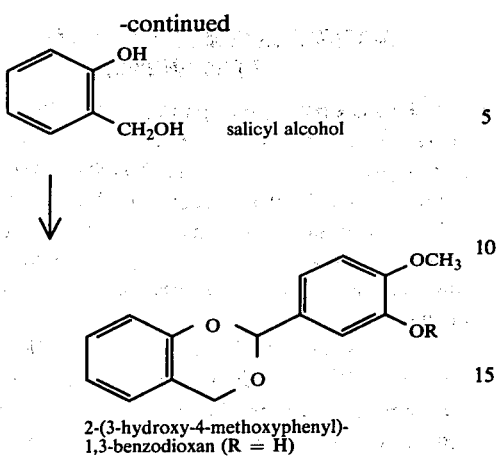

salicyl alcohol 2-(3-hydroxy-4-methoxyphenyl)-
1,3-benzodioxan (R = H)

where R = H or a blocking group and R' = an alkyl.

The benzodioxan can be treated with the appropriate alkali to convert it to the salt of any physiologically acceptable metal cation such as an alkali or alkali earth metal. Exemplary salts would include the $Na^+$, $K^+$, $Mg^{+2}$, and $Ca^{+2}$. These salts can also be prepared directly during the saponification of the ester as mentioned above.

The neutral benzodioxan is readily soluble in ethanol at room temperature. It is also soluble in water and aqueous solutions at concentrations up to about 0.030%, which is above the normal level of usage. Aqueous solutions are most easily prepared by predissolving the compound in a solvent such as ethanol and then adding it to water. The benzodioxan salts of course can be dissolved directly in water in relatively high concentrations.

Preliminary taste tests indicate that the novel sweet compound in neutral form is approximately 3,000 times sweeter than sucrose with full expression of sweetness requiring 2-3 seconds. This time can be reduced about 50% by addition of about 1 mg./ml. of sodium acetate to dilute solutions of the compound. The salt forms are slightly less sweet, but have the advantage of requiring less time to attain full expression. In either form, sweetness tends to linger briefly. When tasted as a solid or concentrated solution, the sweetener produces a flavor similar to licorice, but this flavor is not observed in dilute solutions at normal level of usage.

The expressions "effective amount" and "sweetening amount" are defined herein to include any level of sweetener which imparts detectable sweetness to the medium in which it is incorporated. In general usage, the amount of sweetener will vary from about 0.001% to about 0.1% (w/w basis), with the preferred amount being in the range of about 0.002 to 0.010% (w/w basis).

The expressions "ingestible substance" and "ingestible composition" are used herein interchangeably to refer to any substance or composition which is normally placed into the mouth of a human or animal for the purpose of producing some effect therein or for passing therethrough into the lower portions of the alimentary canal. Exemplary ingestible substances which can be sweetened with the instant additives are table foods, beverages, desserts, candies, chewing gum, orally administered medicinal preparations, and the like. It is understood that the sweetener can either be added directly to these substances or in association with any of the well known, physiologically acceptable, liquid and solid vehicles and carriers.

The following examples are intended only to further illustrate the invention and are not intended to limit the scope of the invention which is defined by the claims.

EXAMPLE 1

A. Preparation of 3-chloroacetoxy-4-methoxybenzaldehyde (hydroxyl blocking reaction)

A stirred mixture containing 108 g. (710 mmol.) of 3-hydroxy-4-methoxybenzaldehyde, 500 ml. of chloroform, and 125 ml. of collidine was kept below 10° C., treated dropwise with 70 ml. (800 mmol.) of chloroacetyl chloride over a 1-hour period, and then stirred 2 hours at 25° C. The solution was serially extracted with 500-ml. portions of water, 0.3N HCl, and water (2×). Chloroform was evaporated and crude 3-chloroacetoxy-4-methoxybenzaldehyde was recrystallized from diethyl ether (147 g., 91%), m.p. 88°-89° C.

B. Preparation of 3-chloroacetoxy-4-methoxybenzaldehyde dimethyl acetal (intermediate acetal formation)

A solution containing 24 g. (105 mmol.) of the product of Example 1A, 14.5 g. (136 mmol.) of trimethylorthoformate, and 1.5 g. (7.9 mmol.) of toluenesulfonic acid monohydrate in 300 ml. of benzene was stirred and refluxed in a 500-ml. r.b. flask connected to a Soxhlet extractor and protected from moisture. The 33 × 94 mm. extraction thimble contained 50 g. of Davison molecular sieve 4A (14-30 mesh). Formation of the intermediate acetal was complete after 1 hour, as judged by thin-layer chromatography (TLC) (9:1, benzene:-diethyl ether), whereupon the solution was cooled to 40°-45° C.

C. Preparation of 2-(3-chloroacetoxy-4-methoxyphenyl)-1,3-benzodioxan

The intermediate acetal solution prepared in Example 1B was diluted with 200 ml. of benzene, and treated with 13 g. (105 mmol.) of o-hydroxybenzyl alcohol. Reflux through the molecular sieve was resumed for 1.5 hours; then the solution was cooled, treated with 2 ml. of pyridine, and diluted to 1,000 ml. with ethyl acetate. The organic layer was extracted with 500-ml. portions of dilute aqueous cupric sulfate and water, dried, and evaporated. The crystalline residue was refluxed 2-3 minutes in 350 ml. of methanol, chilled to 0° C., and filtered to yield the benzodioxan (21.95 g., 62%), m.p. 117°-118° C.

D. Preparation of 2-(3-hydroxy-4-methoxyphenyl)-1,3-benzodioxan

A 30-g. portion of the benzodioxan compound prepared in Example 1C was dissolved in 300 ml. of warm benzene, diluted with 600 ml. of methanol containing 70 mmol. of barium methoxide, and then stored 18 hours at 5° C. After adding 10 g. of ammonium acetate, volatiles were evaporated and the residue was extracted with two 500-ml. portions of chloroform. The chloroform was washed once with 500 ml. of water, the water was reextracted with 500 ml. of chloroform, and the combined chloroform extracts were washed once with 300 ml. of water. Evaporation and crystallization from diethyl ether-n-hexane gave the neutral form of the novel sweet compound (23 g., 95%), m.p. 105°-106° C.

EXAMPLE 2

Preparation of the sodium salt of 2-(3-hydroxy-4-methoxyphenyl)-1,3-benzodioxan

258 Milligrams of the crystalline sweetener prepared in Example 1D was slurried in 80 ml. of deionized water. The slurry was treated with 9.8 ml. of 0.1N NaOH, protected from light, and stirred 1 hour at 25° C. The solution was then made to a volume of 100 ml., filtered, and stored at +5° C.

EXAMPLE 3

Reference solutions of sucrose in deionized water at levels of 3%, 4%, 5%, and 6% (w/v) were prepared. 0.002% Solutions of the sweet compound of Example 1D were prepared by adding 0.2 ml. of a 10 mg./ml. stock solution of the compound in 95% ethanol to 100 ml. of deionized water. All solutions were held at room temperature (22°-24° C.) for 1 hour before tasting.

At intervals of 4-6 hours, each of five persons tasted a single sucrose solution, rinsed his mouth with deionized water, and then tasted the 0.002% sweetener solution. Sweetness was scored at less than, equal to, or greater than the sucrose solution provided. All individuals scored the 0.002% sweetener solution as isosweet with a 6% sucrose solution.

EXAMPLE 4

A 2-ml. portion of the benzodioxan sodium salt solution prepared in Example 2 was diluted with 125 ml. of deionized water to yield approximately a 0.004% solution. This solution of the salt form was judged to be approximately isosweet with a 0.002% solution of the neutral sweetener.

It is understood that the foregoing detailed description is given merely by way of illustration and that modifications and variations may be made therein without departing from the spirit and scope of the invention.

We claim:

1. A sweet compound of the formula

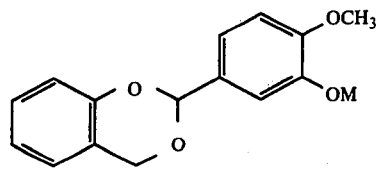

where M is hydrogen or a physiologically acceptable metal cation.

2. The sweet compound as described in claim 1 wherein M is hydrogen.

3. The sweet compound as described in claim 1 wherein M is an alkali metal cation.

4. The sweet compound as described in claim 3 wherein M is selected from the group of $Na^+$ and $K^+$.

5. The sweet compound as described in claim 1 wherein M is an alkali earth metal cation.

6. A composition comprising a food substance and an effective amount of a sweet compound of the formula

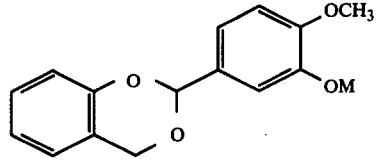

where M is hydrogen or a physiologically acceptable metal cation.

7. The composition as described in claim 6 wherein said food substance is a solid food.

8. The composition as described in claim 6 wherein said food substance is a beverage.

9. The composition as described in claim 6 wherein said food substance is chewing gum.

* * * * *